United States Patent [19]

Mitrowsky et al.

[11] Patent Number: 4,499,023
[45] Date of Patent: Feb. 12, 1985

[54] PROCESS FOR SEPARATING TECHNICALLY PURE 2,4-DIISOCYANATOTOLUENE OR ISOMER MIXTURES HAVING AN INCREASED CONTENT OF 2,4-DIISOCYANATOTOLUENE FROM ISOMER MIXTURES OF 2,4- AND 2,6-DIISOCYANATOTOLUENE

[75] Inventors: Alexander Mitrowsky, Dormagen; Adolf Wissner, Leverkusen; Werner Hauser, Odenthal, all of Fed. Rep. of Germany

[73] Assignee: Bayer Aktiengesellschaft, Leverkusen, Fed. Rep. of Germany

[21] Appl. No.: 493,869

[22] Filed: May 12, 1983

[30] Foreign Application Priority Data

May 29, 1982 [DE] Fed. Rep. of Germany ....... 3220439

[51] Int. Cl.$^3$ .............................................. C07C 71/00
[52] U.S. Cl. .............................................. 260/453 SP
[58] Field of Search ........................ 260/453 SP, 707

[56] References Cited

U.S. PATENT DOCUMENTS 3,217,024 11/1965 Park et al. ........................... 260/45.3
4,246,187 1/1981 Yabroff ........................ 260/453 SP Primary Examiner—Alan Siegel
Attorney, Agent, or Firm—Gene Harsh; Joseph C. Gil; Lyndanne M. Whalen

[57] ABSTRACT

Technically pure 2,4-diisocyanatotoluene or an isomer mixture having an increased 2,4-diisocyanatotoluene content is obtained from an isomer mixture of 2,4- and 2,6-diisocyanatotoluene. The 2,4- and 2,6-diisocyanatotoluene mixture is first cooled to a temperature of from 4° to 9° C. and further cooled to between −2° to −6° C. at a rate of 0.5° to 3° C. per hour. The temperature of the mixture is maintained at that temperature for at least 30 minutes. Any liquid present is removed and the solid remaining is then melted. Melting is preferably carried out by heating the solid at a rate of 0.5° to 3° C. per hour until the remaining solid has a 2,4-diisocyanatotoluene content of at least 98%. The liquid melt is removed and the solid having the desired 2,4-diisocyanatotoluene content is then melted.

5 Claims, No Drawings

PROCESS FOR SEPARATING TECHNICALLY PURE 2,4-DIISOCYANATOTOLUENE OR ISOMER MIXTURES HAVING AN INCREASED CONTENT OF 2,4-DIISOCYANATOTOLUENE FROM ISOMER MIXTURES OF 2,4- AND 2,6-DIISOCYANATOTOLUENE

BACKGROUND OF THE INVENTION

This invention relates to an improved process for isolating technically pure 2,4-diisocyanatotoluene or isomer mixtures having an increased content of 2,4-diisocyanatotoluene from isomer mixtures of 2,4- and 2,6-diisocyanatotoluene by single-stage crystallization in a tube crystallizer.

Mixtures of 2,4- and 2,6-isomers generally accumulate during the commercial production of diisocyanatotoluene (an important starting material for the production of polyurethane plastics). However, the two isomers do not behave the same way chemically during further processing. This is evidenced by the fact that products having different properties are formed when the isomer composition of the isomer mixtures is varied. In many cases, it is advisable to use technically pure 2,4-diisocyanatotoluene (i.e. 2,4-diisocyanatotoluene having a purity of at least 98 wt. %) in the production of polyurethane plastics.

Since adjustment of the particular isomer ratio and use of the isomer mixture without an additional purification step are both complicated and expensive, there have been many attempts to achieve technically workable methods for isomer separation, particularly on the basis of crystallization.

For example, U.S. Pat. No. 3,217,024 describes a two-stage crystallization process in which a 90–94% 2,4-diisocyanatotoluene and a 65/35-isomer mixture are obtained from an 80/20-isomer mixture in the first step. The still impure 2,4-isomer (90–94%) is brought to the required purity in a second step. This complicated procedure appears to be necessary in view of the pronounced tendency of 2,4-diisocyanatotoluene to crystallize from isomer mixtures only after radical super cooling accompanied by the formation of inclusions. U.S. Pat. No. 4,246,187 discloses a process which attempted to overcome these difficulties by allowing only 10 to 20 wt. % of the 2,4-diisocyanatotoluene to crystallize out. This crystallized fraction was subsequently separated by means of a centrifuge. This process for separation or enrichment of the isomers also involves considerable technical outlay.

The so-called "drip process" described in "Chemische Technologie", 3, Carl Hanser Verlag, Munich, (1959), pages 812–813, for the separation of isomers from nucleus-chlorinated compounds cannot be satisfactorily applied to the separation of diisocyanatotoluene isomers because cooling to the softening point of the eutectic results in unsatisfactory isomer separation and poor volume/time yields.

SUMMARY OF THE INVENTION

It is an object of the present invention to provide a process for separating technically pure 2,4-diisocyanatotoluene from 2,4- and 2,6-diisocyanatotoluene isomer mixtures.

It is also an object of the present invention to provide a process for separating technically pure 2,4-diisocyanatotoluene or an isomer mixture having increased 2,4-diisocyanatotoluene content from an isomer mixture of 2,4- and 2,6-diisocyanatotoluene which is both efficient and technically simple.

These and other objects which will be apparent to those skilled in the art are accomplished by cooling in a tube crystallizer an isomer mixture of 2,4- and 2,6-diisocyanatotoluene to a temperature of from 4° to 9° C., further cooling the mixture to between −2° and −6° C. at a rate of 0.5° to 3° C. per hour and maintaining the mixture at that temperature for at least 30 minutes. Any liquid present in the thus-cooled mixture is then removed. The solid remaining in the tube crystallizer is then melted. Melting is preferably carried out by heating the solid at a rate of 0.5° to 3° C. per hour until the remaining solid has a 2,4-diisocyanatotoluene content of at least 98%. This technically pure 2,4-diisocyanatotoluene (i.e., remaining solid) is subsequently isolated from the tube crystallizer.

DETAILED DESCRIPTION OF THE INVENTION

The present invention relates to a process for the separation of pure 2,4-diisocyanatotoluene or of isomer mixtures having an increased content of 2,4-diisocyanatotoluene from isomer mixtures of 2,4- and 2,6-diisocyanatotoluene. This process is carried out in a tube crystallizer made up of one or more vertically arranged, parallel tubes, on which and between which cooling and heating media are able to flow uniformly and freely. The isomer mixture used as starting material is first cooled to a temperature of from +4° C. to +9° C. The mixture is then further cooled to between −2° and −6° C. at a rate of 0.5 to 3° C. per hour and maintained at a temperature in that range for at least 30 minutes. The mother liquor present is then allowed to run off at that temperature and the solid remaining in the tube crystallizer is melted by heating.

The solid accumulating in this process has a considerably increased content of 2,4-diisocyanatotoluene compared to the starting mixture. Thus, it is possible to obtain in the form of a solid an isomer mixture made up of approximately 80 wt. % 2,4- and approximately 20 wt. % of 2,6-diisocyanatotoluene from an isomer mixture made up of 65 wt. % 2,4- and 35 wt. % 2,6-diisocyanatotoluene solely by the selective crystallization which takes place in the cooling steps of the present invention and isolation of the solid thus obtained from the tube crystallizer after melting.

More extensive isomer separation may readily be achieved by gradually melting part of the solid present in the tube crystallizer at a rate of 0.5° to 3° C. per hour. The liquid formed during this melting is then continuously run off, until the solid remaining in the tube crystallizer has the desired content of 2,4-diisocyanatotoluene. In this way, it is possible for example to start with an isomer mixture containing from 75 to 85 wt. % (preferably from 78 to 82 wt. %) 2,4-diisocyanatotoluene and from 15 to 25 wt. % (preferably from 18 to 22 wt. %) 2,6-diisocyanatotoluene and obtain technically pure 2,4-diisocyanatotoluene (i.e. 2,4-diisocyanatotoluene having a purity of at least 98 wt. % and preferably of at least 99 wt. %) in the form of a solid remaining in the crystallizer and to isolate it in liquid form after melting.

Diisocyanatotoluene isomer mixtures containing from about 65 to about 85 wt. % 2,4-diisocyanatotoluene and from about 15 to about 35 wt. % 2,6-diisocyanatotoluene are generally used as the starting material in the process of the present invention. The mixtures used as starting material preferably contain from 75 to 85 wt. % and most preferably from 78 to 82 wt. % 2,4-diisocyanatotoluene and from 15 to 25 wt. % and most preferably from 18 to 22 wt. % 2,6-diisocyanatotoluene.

In carrying out the process of the present invention, the starting mixture may be rapidly cooled in the tube crystallizer until crystallization begins, i.e. to a temperature of from +4° C. to +9° C. and preferably to a temperature of from +5° C. to +7° C., without any special precautionary measures (for example maintaining a certain temperature gradient). After the desired temperature has been reached, the mixture is further cooled to a temperature of from about −2° C. to about −6° C. and preferably to a temperature of from −3° C. to −5° C. at a rate of 0.5° to 3° C. per hour. During this gradual cooling, it is essential that the melting point of the eutectic (−7° C.) not be reached because only on this condition is optimal isomer separation possible. Substantially complete temperature equalization in the tube crystallizer is brought about by maintaining the temperature at −2° to −6° C. for at least 30 minutes and preferably from 1 to 3 hours. During this period, the temperature is kept constant by a cooling medium. After the temperature maintenance period, the mother liquor is run off and collected in, for example, a vessel equipped with a recirculating pump.

In one embodiment of the process of the present invention, the solid still present in the crystallizer is isolated by melting in the manner described above. However, in the preferred embodiment of the process of the present invention the solid remaining in the tube crystallizer after the mother liquor has been run off is gradually heated at a rate of 0.5° to 3° C. per hour. The liquid which forms during this gradual heating is continuously run off, until the solid still remaining in the tube crystallizer has the desired content of 2,4-diisocyanatotoluene. Where the starting mixture contains from 78 to 82 wt. % 2,4-diisocyanatotoluene, it may be assumed that the solid remaining in the tube crystallizer is technically pure 2,4-diisocyanatotoluene if the combined mother liquors and melts have a 2,4-diisocyanatotoluene content of at least 63 wt. %, preferably from 63 to 68 wt. % and, most preferably from 64 to 66 wt. %. If more off-runnings accumulate thereafter, they may be separately collected and used for the next batch. To isolate the technically pure 2,4-diisocyanatotoluene, the gradual melting process may generally be terminated when the content of 2,4-diisocyanatotoluene in the combined mother liquor and melts is 63 wt. % or higher. The outlet is then closed and the material still present in the crystallizer is melted and run off into a storage tank for technically pure 2,4-diisocyanatotoluene. The required purity may of course, be influenced by closing the outlet at an earlier or later stage.

As already explained, the tube crystallizer used in the process of the present invention is at least one, preferably several, upright (preferably vertically arranged) parallel tubes on which and between which cooling and heating medium is able to flow uniformly and freely. In general, the individual tubes are between 1 and 8 meters and preferably between 3 and 6 meters long for an internal diameter of from 1 to 8 cm and preferably from 2 to 5 cm. However, the number of tubes and their dimensions are by no means critical to the invention and are largely determined by the required capacity of the apparatus. Thus, it is possible to use a single tube only 50 cm long as a laboratory apparatus. A suitable liquid or air or another gas may be used as the heating and cooling medium. Both the liquid and the gas are forcibly circulated. The heat transfer medium may be cooled by liquid ammonia or even haloalkanes such as e.g. $CClF_3$ or $CCl_2F_2$ with the heating exchange taking place through a corresponding cooling register. An organic heat carrier or steam may be used as the heating medium with the heat transfer taking place through a corresponding heating register. A suitable precision control system must be present for energy transfer to enable the small temperature gradients required in the cooling and heating phase to be achieved.

The percentages quoted in the following Examples are percentages by weight.

EXAMPLES

Example 1

The tube crystallizer used had a volume of 20 cubic meters. The crystallizer was made up of a jacketed tube nest of 1700 parallel, vertically arranged tubes which were 6 meters long with an internal diameter of 5 cm. The nest of tubes was connected at its upper end to a common inlet and at its lower end to a common outlet. In addition, the tube crystallizer was equipped with 3 thermocouples arranged at various levels of the tubes. The heat transfer medium was air, the cooling medium was liquid ammonia and the heating medium was steam.

20 m$^3$ of a mixture of 80.5% of 2,4-diisocyanatotoluene and 19.5% of 2,6-diisocyanatotoluene were introduced into the above-described crystallizer at a temperature of around 30° C. The mixture was then cooled to a temperature of 6° C. over a period of 5 hours. Partial crystallization began at that temperature. The mixture was then cooled to −5° C. at a rate of 1° C. per hour and kept at that temperature for 1 hour. The outlet was then opened and the mother liquor left to run off while the temperature of −5° C. was maintained for another 4 hours. The solid remaining in the tube crystallizer was then heated to 21° C. at a rate of 1° C. per hour. The melt which formed was continuously run off. The mixture of the mother liquor with the run off melt had a 2,4-diisocyanatotoluene content of 68.7% and a 2,6-diisocyanatotoluene content of 31.3%. After the outlet had been closed, the solid still present in the crystallizer was melted and run off into a storage tank for technically pure 2,4-diisocyanatotoluene. The product had a 2,4-diisocyanatotoluene content of 99.2%.

Example 2

A mixture of 79.2% of 2,4-diisocyanatotoluene and 80.8% of 2,6-diisocyanatotoluene was introduced into a 7 liter capacity test crystallizer in which the tube was 3.7 meters long with an internal diameter of 5 cm. The mixture was cooled from the starting temperature of 25° C. to +6° C. over a period of 3 hours. The mixture was then cooled to −5° C. at a rate of 1° C. per hour. The temperature of −5° C. was then maintained for 2 hours. The mother liquor was then run off over a period of another 3 hours at −5° C. Finally, the solid substance remaining in the crystallizer was heated to 21° C. at a rate of 1° C. per hour. The melt which formed was continuously run off. Thereafter, the mixture of mother liquor and melt had a 2,4-diisocyanatotoluene content of 65.3%. The technically pure 2,4-diisocyanatotoluene ultimately obtained had a purity of 99.5%.

The heat transfer medium used in this Example was methanol which was cooled by a cryostat and heated by a thermostat.

Example 3

20 m³ of an isomer mixture of 65% of 2,4- and 35% of 2,6-diisocyanatotoluene were introduced into the tube crystallizer described in Example 1. The isomer mixture was then cooled from the starting temperature of +25° C. to +6° C. (incipient crystallization) over a period of 3 hours. The mixture was then cooled to −4° C. at a rate of 1° C. per hour and then left at that temperature for 2 hours. The mother liquor was then run off over a period of 5 hours during which the temperature of −4° C. was maintained.

The solid then remaining in the crystallizer was melted and run off into a storage tank. 79.2% was 2,4-diisocyanatotoluene and 20.8% was 2,6-diisocyanatotoluene.

Although the invention has been described in detail in the foregoing for the purpose of illustration, it is to be understood that such detail is solely for for that purpose and that variations can be made therein by those skilled in the art without departing from the spirit and scope of the invention except as it may be limited by the claims.

What is claimed is:

1. A process for separating pure 2,4-diisocyanatotoluene or an isomer mixture having an increased 2,4-diisocyanatotoluene content from an isomer mixture of 2,4- and 2,6-diisocyanatotoluene in a tube crystallizer comprising:
   (a) cooling the isomer mixture of 2,4- and 2,6-diisocyanatotoluene to a temperature of from 4° to 9° C.,
   (b) further cooling the isomer mixture of (a) to between −2° and −6° C. at a rate of 0.5° to 3° C. per hour,
   (c) maintaining the mixture of (b) at a temperature of from −2° to −6° C. for at least 30 minutes,
   (d) removing any liquid present in the mixture of (c), and
   (e) melting any solid remaining in the tube crystallizer.

2. The process of claim 1 wherein the tube crystallizer is made up of more than one tube.

3. The process of claim 2 wherein the tube crystallizer is made up of vertically arranged parallel tubes.

4. The process of claim 1 wherein the melting step (e) is carried out by heating the solid at a rate of 0.5° to 3° C. per hour until the remaining solid has a 2,4-diisocyanatotoluene content of at least 98% and subsequently isolating the technically pure 2,4-diisocyanatotoluene from the tube crystallizer.

5. The process of claim 1 wherein the isomer mixture of 2,4- and 2,6-diisocyanatotoluene used as the starting material is 75 to 85 wt. % 2,4-diisocyanatotoluene and 15 to 25 wt. % 2,6-diisocyanatotoluene.

* * * * *